US009085795B2

(12) United States Patent
Day

(10) Patent No.: US 9,085,795 B2
(45) Date of Patent: Jul. 21, 2015

(54) METHODS FOR SCREENING CANDIDATE AGENTS FOR MODULATING PRORENIN AND RENIN, ASSAYS FOR DETECTING PRORENIN AND ANTIBODIES

(75) Inventor: Duane E. Day, Novi, MI (US)

(73) Assignee: MOLECULAR INNOVATIONS, INC., Novi, MI (US)

(*) Notice: Subject to any disclaimer, the term of this patent is extended or adjusted under 35 U.S.C. 154(b) by 395 days.

(21) Appl. No.: 12/700,126

(22) Filed: Feb. 4, 2010

(65) Prior Publication Data

US 2010/0196367 A1 Aug. 5, 2010

Related U.S. Application Data

(60) Provisional application No. 61/149,834, filed on Feb. 4, 2009, provisional application No. 61/150,462, filed on Feb. 6, 2009, provisional application No. 61/152,285, filed on Feb. 13, 2009, provisional application No. 61/159,233, filed on Mar. 11, 2009, provisional application No. 61/160,011, filed on Mar. 13, 2009, provisional application No. 61/234,424, filed on Aug. 17, 2009.

(51) Int. Cl.
*A61K 39/395* (2006.01)
*C07K 16/36* (2006.01)
*G01N 33/53* (2006.01)
*C12Q 1/37* (2006.01)
*C07K 16/40* (2006.01)
*G01N 33/573* (2006.01)

(52) U.S. Cl.
CPC . *C12Q 1/37* (2013.01); *C07K 16/40* (2013.01); *G01N 33/573* (2013.01); *C07K 2317/76* (2013.01); *G01N 2333/95* (2013.01); *G01N 2500/02* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 5,225,539 | A | 7/1993 | Winter |
| 5,585,089 | A | 12/1996 | Queen et al. |
| 5,693,761 | A | 12/1997 | Queen et al. |
| 5,693,762 | A | 12/1997 | Queen et al. |
| 5,859,205 | A | 1/1999 | Adair et al. |
| 5,945,512 | A | 8/1999 | Murakami et al. |
| 6,407,213 | B1 | 6/2002 | Carter et al. |
| 6,900,020 | B2* | 5/2005 | Ishida et al. ............ 435/7.1 |
| 7,064,244 | B2 | 6/2006 | Jakobovits et al. |
| 2003/0059946 | A1 | 3/2003 | Pandian |
| 2007/0253949 | A1* | 11/2007 | Golz et al. ............ 424/133.1 |

FOREIGN PATENT DOCUMENTS

| | | |
|---|---|---|
| EP | 0171496 A2 | 2/1986 |
| EP | 0173494 A2 | 3/1986 |
| EP | 0239400 A2 | 9/1987 |
| GB | 2177096 A | 1/1987 |
| WO | 92/06193 A1 | 4/1992 |
| WO | 94/04678 A1 | 3/1994 |
| WO | 96/33735 A1 | 10/1996 |
| WO | 96/34096 A1 | 10/1996 |
| WO | 97/49805 A2 | 12/1997 |
| WO | 03/014161 A2 | 2/2003 |

OTHER PUBLICATIONS

Bost et al., Immunol. Invest. 17:577-586, 1988.*
Bendayan, J. Histochem. Cytochem. 43: 881-886, 1995.*
Schumacher M. et al., "A direct immunoradiometric assay for human plasma prorenin: concentrations in cycling women and in women taking oral contraceptives," J. Clin. Endocrinol. Metab., 1992, vol. 75, No. 2—(Abstract Only).
De Bruin, Rene A. et al., "Validation of a New Automated Renin Assay," Clinical Chemistry, 2004, vol. 50, No. 11, pp. 2111-2116.
Cohen, Pascale et al., "New monoclonal antibodies directed against the propart segment of human prorenin as a tool for the exploration of prorenin conformation," Journal of Immunological Methods, 1995, vol. 184, pp. 91-100.
Streltov, Victor A., et al., "Structure of a shark IgNAR antibody varible domain and modeling of an early-developmental isotype," Protein Science, 2005, vol. 14, pp. 2901-2909.
Schalekamp, Maarten A.D.H. et al., "Newly developed renin and prorenin assays and the clinical evalution of renin inhibitors," Journal of Hypertension, 2008, vol. 26, pp. 928-937.
Paschalidou, Katherine et al., "Highly sensitive intramolecularly quenched fluorogenic substrates for renin based on the combination of L-2-amino-3-(7-methoxy-4-coumaryl)propionic acid with 2,4-dinitrophenyl groups at various positions," Biochem. J. 2004, vol. 382, pp. 1031-1038.
Muyldermans, Serge, "Single domain camel antibodies: current status," Reviews in Molecular Biotechnology, 2001, vol. 74, pp. 277-302.
Mercure Chantal et al., "Molecular Analysis of Human Prorenin Prosegment Variants in Vitro and in Vivo," The Journal of Biological Chemistry, 1995, vol. 270, No. 27, pp. 16355-16359.
Nguyen, Genevieve et al., "Pivotal Role of the Renin/Prorenin Receptor in Angiotensin II Production and Cellular Response to Renin," The Journal of Clinical Investigation, 2002, vol. 109, No. 11, pp. 1417-1427.
Teng, Nelson N.H., et al., "Construction and Testing of Mouse-Human Heteromyelomas for Human Monocolonal Antibody Production," Proc. Natl. Acad. Sci. U.S.A.,1983, vol. 80, pp. 7308-7312.
Morrison, Sherie L., et al., "Chimeric Human Antibody molecules: Mouse Antigen-Binding Domains with Human Constant Region Domains," Proc. Natl. Acad. Sci. U.S.A., 1984, vol. 81, pp. 6851-6855.

(Continued)

*Primary Examiner* — Phillip Gambel
(74) *Attorney, Agent, or Firm* — Fitzpatrick, Cella, Harper & Scinto

(57) ABSTRACT

The present invention relates to antibodies that bind to prorenin. In particular, the invention relates to monoclonal antibodies that bind to prorenin and inhibit the activation of prorenin. The antibodies of the invention are useful for screening for candidate agents that inhibit the activation of prorenin and candidate agents the modulate the activity of renin. The antibodies are also useful as diagnostics and for treating disease states.

18 Claims, 10 Drawing Sheets

(56) References Cited

OTHER PUBLICATIONS

Altschul et al., "Basic Local Alignment Search Tool," J. Mol. Biol., vol. 215, pp. 403-410 (1990).

Hemmer et al., Contribution of individual amino acids within MHC molecule or antigenic peptide to TCR ligand potency, J. Immunol. Jan. 15, 2000; 164(2): 861-71.

Potter et al., Differential processing and presentation of the H-2D(b)-restricted epitope from two different strains of influenza virus nucleoprotein, J. Gen Virol. 2001 82: 1069-74.

Krop et al., Evaluation of a direct prorenin assay making use of a monoclonal antibody directed against residues 32-39 of the prosegment, J. Hyerptens. Nov. 2011; 29(11): 2138-46.

Deinum et al., "Probing epitopes on human prorenin during its proteolytic and non-proteolytic activation," Biochim. Biophys. ACTA 1388(2): 386-396 (Nov. 10, 1998).

Gaillard et al., "Analysis of inactive renin by renin profragment monoclonal antibodies," Febs Letters 207(1): 100-104 (Oct. 20, 1986).

Green et al., "Antigen-specific human monoclonal antibodies from mice engineered with human Ig heavy and light chain YACs," Nature Genetics, vol. 7, pp. 13-21 (May 1994).

Hirose et al., "In vitro biosynthesis of human renin and identification of plasma inactive renin as an activation intermediate," J. Biol. Chem. 260(30) : 16400-16405 (1985).

Ishizuka et al., "Characterization of monoclonal antibodies against human prorenin profragment and identification of active prorenins in plasma," J. Biochem. 106(3): 430-435 (Jan. 1, 1989).

Kohler and Milstein, "Continuous cultures of fused cells secreting antibody of predefined specificity," Nature 256:495-97 (1975).

Kozbor et al., "The production of monoclonal antibodies from human lymphocytes," Immunology Today, vol. 4, No. 3, pp. 72-79 (1983).

Morrison, "Transfectomas Provide Novel Chimeric Antibodies," Science, vol. 229, pp. 1202-1207 (Sep. 20, 1985).

Myers et al., "Optimal Alignments in Linear Space," Comput. Appl. Biosci., vol. 4, No. 1, pp. 11-17 (1988).

Needleman et al., "A General Method Applicable to the Search for Similarities in the Amino Acid Sequence of Two Proteins," J. Mol. Biol., vol. 48, pp. 443-453 (1970).

Oi et al., "Chimeric Antibodies," BioTechniques, vol. 4, No. 3, pp. 214-221 (1986).

Olsson et al., "Human-Human Monoclonal Antibody-Producing Hybridomas: Technical Aspects," Methods in Enzymology, vol. 92, pp. 3-16 (1983).

Takeda et al., "Construction of chimaeric processed immunoglobulin genes containing mouse variable and human constant region sequences," Nature, vol. 314, pp. 452-454 (Apr. 1985).

Supplementary European Search Report and European Search Opinion issued in European Patent Application No. 10739124.5 dated Jan. 7, 2013—11 pages.

\* cited by examiner

Western Blot 10% SDS PAGE

1) Human prorenin (0.5 µg)
2) Human renin (0.5 µg)

Figure 5

Screening for Sequence to Positive Peptides 4
4B5-E3 Monoclonal Antibody

Peptide 4 - 3 Sequences (T2951-1, T2951-2, T2951-3)
ARLGPEWSQ, ARLGPEWS, ARLGPEW

FIGURE 8A

LPTDTTTFKRIFLKRMPSIRESLKERGVDMARLGPEWSQPMKRLTLGNTTSSVILTNYMDTQYYG
EIGIGTPPQTFKVVFDTGSSNVWVPSSKCSRLYTACVYHKLFDASDSSSYKHNGTELTLRYSTGT
VSGFLSQDIITVGGITVTQMFGEVTEMPALPFMLAEFDGVVGMGFIEQAIGRVTPIFDNIISQGVLK
EDVFSFYYNRDSENSQSLGGQIVLGGSDPQHYEGNFHYINLIKTGVWQIQMKGVSVGSSTLLCED
GCLALVDTGASYISGSTSSIEKLMEALGAKKRLFDYVVKCNEGPTLPDISFHLGGKEYTLTSADY
VFQESYSSKKLCTLAIHAMDIPPPTGPTWALGATFIRKFYTEFDRRNNRIGFALAR

FIGURE 8B

CTCCCGACAGACACCACCACCTTTAAACGGATCTTCCTCAAGAGAATGCCCTCAATCCGAGA
AAGCCTGAAGGAACGAGGTGTGGACATGGCCAGGCTTGGTCCCGAGTGGAGCCAACCCATG
AAGAGGCTGACACTTGGCAACACCACCTCCTCCGTGATCCTCACCAACTACATGGACACCCA
GTACTATGGCGAGATTGGCATCGGCACCCCACCCCAGACCTTCAAAGTCGTCTTTGACACTG
GTTCGTCCAATGTTTGGGTGCCCTCCTCCAAGTGCAGCCGTCTCTACACTGCCTGTGTGTATC
ACAAGCTCTTCGATGCTTCGGATTCCTCCAGCTACAAGCACAATGGAACAGAACTCACCCTC
CGCTATTCAACAGGGACAGTCAGTGGCTTTCTCAGCCAGGACATCATCACCGTGGGTGGAAT
CACGGTGACACAGATGTTTGGAGAGGTCACGGAGATGCCCGCCTTACCCTTCATGCTGGCCG
AGTTTGATGGGGTTGTGGGCATGGGCTTCATTGAACAGGCCATTGGCAGGGTCACCCCTATC
TTCGACAACATCATCTCCCAAGGGGTGCTAAAAGAGGACGTCTTCTCTTTCTACTACAACAG
AGATTCCGAGAATTCCCAATCGCTGGGAGGACAGATTGTGCTGGGAGGCAGCGACCCCCAG
CATTACGAAGGGAATTTCCACTATATCAACCTCATCAAGACTGGTGTCTGGCAGATTCAAAT
GAAGGGGGTGTCTGTGGGGTCATCCACCTTGCTCTGTGAAGACGGCTGCCTGGCATTGGTAG
ACACCGGTGCATCCTACATCTCAGGTTCTACCAGCTCCATAGAGAAGCTCATGGAGGCCTTG
GGAGCCAAGAAGAGGCTGTTTGATTATGTCGTGAAGTGTAACGAGGGCCCTACACTCCCCG
ACATCTCTTTCCACCTGGGAG
GCAAAGAATACACGCTCACCAGCGCGGACTATGTATTTCAGGAATCCTACAGTAGTAAAAA
GCTGTGCACACTGGCCATCCACGCCATGGATATCCCGCCACCCACTGGACCCACCTGGGCCC
TGGGGGCCACCTTCATCCGAAAGTTCTACACAGAGTTTGATCGGCGTAACAACCGCATTGGC
TTCGCCTTGGCCCGCTGA

SEQUENCE LISTING

```
<160> NUMBER OF SEQ ID NOS: 23

<210> SEQ ID NO 1
<211> LENGTH: 383
<212> TYPE: PRT
<213> ORGANISM: Homo sapiens

<400> SEQUENCE: 1

Leu Pro Thr Asp Thr Thr Thr Phe Lys Arg Ile Phe Leu Lys Arg Met
1               5                   10                  15

Pro Ser Ile Arg Glu Ser Leu Lys Glu Arg Gly Val Asp Met Ala Arg
            20                  25                  30
```

Leu Gly Pro Glu Trp Ser Gln Pro Met Lys Arg Leu Thr Leu Gly Asn
    35                  40                  45

Thr Thr Ser Ser Val Ile Leu Thr Asn Tyr Met Asp Thr Gln Tyr Tyr
 50                  55                  60

Gly Glu Ile Gly Ile Gly Thr Pro Pro Gln Thr Phe Lys Val Val Phe
 65                  70                  75                  80

Asp Thr Gly Ser Ser Asn Val Trp Val Pro Ser Ser Lys Cys Ser Arg
                 85                  90                  95

Leu Tyr Thr Ala Cys Val Tyr His Lys Leu Phe Asp Ala Ser Asp Ser
                100                 105                 110

Ser Ser Tyr Lys His Asn Gly Thr Glu Leu Thr Leu Arg Tyr Ser Thr
            115                 120                 125

Gly Thr Val Ser Gly Phe Leu Ser Gln Asp Ile Ile Thr Val Gly Gly
130                 135                 140

Ile Thr Val Thr Gln Met Phe Gly Glu Val Thr Glu Met Pro Ala Leu
145                 150                 155                 160

Pro Phe Met Leu Ala Glu Phe Asp Gly Val Val Gly Met Gly Phe Ile
                165                 170                 175

Glu Gln Ala Ile Gly Arg Val Thr Pro Ile Phe Asp Asn Ile Ile Ser
            180                 185                 190

Gln Gly Val Leu Lys Glu Asp Val Phe Ser Phe Tyr Tyr Asn Arg Asp
        195                 200                 205

Ser Glu Asn Ser Gln Ser Leu Gly Gly Gln Ile Val Leu Gly Gly Ser
    210                 215                 220

Asp Pro Gln His Tyr Glu Gly Asn Phe His Tyr Ile Asn Leu Ile Lys
225                 230                 235                 240

Thr Gly Val Trp Gln Ile Gln Met Lys Gly Val Ser Val Gly Ser Ser
                245                 250                 255

Thr Leu Leu Cys Glu Asp Gly Cys Leu Ala Leu Val Asp Thr Gly Ala
            260                 265                 270

Ser Tyr Ile Ser Gly Ser Thr Ser Ser Ile Glu Lys Leu Met Glu Ala
        275                 280                 285

Leu Gly Ala Lys Lys Arg Leu Phe Asp Tyr Val Val Lys Cys Asn Glu
    290                 295                 300

Gly Pro Thr Leu Pro Asp Ile Ser Phe His Leu Gly Gly Lys Glu Tyr
305                 310                 315                 320

Thr Leu Thr Ser Ala Asp Tyr Val Phe Gln Glu Ser Tyr Ser Ser Lys
                325                 330                 335

Lys Leu Cys Thr Leu Ala Ile His Ala Met Asp Ile Pro Pro Pro Thr
            340                 345                 350

Gly Pro Thr Trp Ala Leu Gly Ala Thr Phe Ile Arg Lys Phe Tyr Thr
        355                 360                 365

Glu Phe Asp Arg Arg Asn Asn Arg Ile Gly Phe Ala Leu Ala Arg
    370                 375                 380

<210> SEQ ID NO 2
<211> LENGTH: 1152
<212> TYPE: DNA
<213> ORGANISM: Homo sapiens

<400> SEQUENCE: 2
ctcccgacag acaccaccac ctttaaacgg atcttcctca agagaatgcc ctcaatccga    60
gaaagcctga aggaacgagg tgtggacatg gccaggcttg gtcccgagtg gagccaaccc   120

-continued

```
atgaagaggc tgacacttgg caacaccacc tcctccgtga tcctcaccaa ctacatggac    180
acccagtact atggcgagat tggcatcggc accccacccc agaccttcaa agtcgtcttt    240
gacactggtt cgtccaatgt ttgggtgccc tcctccaagt gcagccgtct ctacactgcc    300
tgtgtgtatc acaagctctt cgatgcttcg gattcctcca gctacaagca caatggaaca    360
gaactcaccc tccgctattc aacagggaca gtcagtggct ttctcagcca ggacatcatc    420
accgtgggtg aatcacggt gacacagatg tttggagagg tcacggagat gcccgccta    480
ccccttcatgc tggccgagtt tgatggggtt gtgggcatgg gcttcattga acaggccatt    540
ggcagggtca ccctatctt cgacaacatc atctcccaag gggtgctaaa agaggacgtc    600
ttctctttct actacaacag agattccgag aattcccaat cgctgggagg acagattgtg    660
ctggaggca cgaccccca gcattacgaa gggaatttcc actatatcaa cctcatcaag    720
actggtgtct ggcagattca aatgaagggg gtgtctgtgg ggtcatccac cttgctctgt    780
gaagacggct gcctggcatt ggtagacacc ggtgcatcct acatctcagg ttctaccagc    840
tccatagaga agctcatgga ggccttggga gccaagaaga ggctgtttga ttatgtcgtg    900
aagtgtaacg agggccctac actccccgac atctctttcc acctgggagg caaagaatac    960
acgctcacca gcgcggacta tgtatttcag gaatcctaca gtagtaaaaa gctgtgcaca   1020
ctggccatcc acgccatgga tatcccgcca ccactggac ccacctgggc cctggggcc     1080
accttcatcc gaaagttcta cacagagttt gatcggcgta caaccgcat tggcttcgcc    1140
ttggcccgct ga                                                        1152
```

<210> SEQ ID NO 3
<211> LENGTH: 8
<212> TYPE: PRT
<213> ORGANISM: Homo sapiens

<400> SEQUENCE: 3

Ala Arg Leu Gly Pro Glu Trp Ser
1               5

<210> SEQ ID NO 4
<211> LENGTH: 14
<212> TYPE: PRT
<213> ORGANISM: Homo sapiens

<400> SEQUENCE: 4

Asp Arg Val Tyr Ile His Pro Phe His Leu Val Ile His Thr
1               5                   10

<210> SEQ ID NO 5
<211> LENGTH: 10
<212> TYPE: PRT
<213> ORGANISM: Homo sapiens

<400> SEQUENCE: 5

Lys Lys His Pro Phe His Leu Val Ile His
1               5                   10

<210> SEQ ID NO 6
<211> LENGTH: 8
<212> TYPE: PRT
<213> ORGANISM: Homo sapiens

<400> SEQUENCE: 6

Ala Arg Leu Gly Pro Glu Trp Ser
1               5

<210> SEQ ID NO 7
<211> LENGTH: 7
<212> TYPE: PRT
<213> ORGANISM: Homo sapiens

<400> SEQUENCE: 7

Ala Arg Leu Gly Pro Glu Trp
1               5

<210> SEQ ID NO 8
<211> LENGTH: 17
<212> TYPE: PRT
<213> ORGANISM: Homo sapiens

<400> SEQUENCE: 8

Lys His Pro Phe His Leu Val Ile His Ala Arg Leu Gly Pro Glu Trp
1               5                   10                  15

Ser

<210> SEQ ID NO 9
<211> LENGTH: 16
<212> TYPE: PRT
<213> ORGANISM: Homo sapiens

<400> SEQUENCE: 9

Lys His Pro Phe His Leu Val Ile His Ala Arg Leu Gly Pro Glu Trp
1               5                   10                  15

<210> SEQ ID NO 10
<211> LENGTH: 43
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylated at this location

<400> SEQUENCE: 10

Leu Pro Thr Asp Thr Thr Thr Phe Lys Arg Ile Phe Leu Lys Arg Met
1               5                   10                  15

Pro Ser Ile Arg Glu Ser Leu Lys Glu Arg Gly Val Asp Met Ala Arg
                20                  25                  30

Leu Gly Pro Glu Trp Ser Gln Pro Met Lys Arg
            35                  40

<210> SEQ ID NO 11
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylated at this location

<400> SEQUENCE: 11

Leu Pro Thr Asp Thr Thr Thr Phe Lys Arg Ile Phe Leu Lys Arg
1               5                   10                  15

<210> SEQ ID NO 12
<211> LENGTH: 15

```
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylated at this location

<400> SEQUENCE: 12

Thr Asp Thr Thr Thr Phe Lys Arg Ile Phe Leu Lys Arg Met Pro
1               5                   10                  15

<210> SEQ ID NO 13
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylated at this location

<400> SEQUENCE: 13

Lys Arg Met Pro Ser Ile Arg Glu Ser Leu Lys Glu Arg Gly Val Asp
1               5                   10                  15

Met

<210> SEQ ID NO 14
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylated at this location

<400> SEQUENCE: 14

Gly Val Asp Met Ala Arg Leu Gly Pro Glu Trp Ser Gln Pro Met Lys
1               5                   10                  15

Arg

<210> SEQ ID NO 15
<211> LENGTH: 14
<212> TYPE: PRT
<213> ORGANISM: Homo sapiens

<400> SEQUENCE: 15

Met Ala Arg Leu Gly Pro Glu Trp Ser Gln Pro Met Lys Arg
1               5                   10

<210> SEQ ID NO 16
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylated at this location

<400> SEQUENCE: 16

Ala Arg Leu Gly Pro Glu Trp Ser Gln Pro Met Lys Arg
1               5                   10
```

```
<210> SEQ ID NO 17
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylated at this location

<400> SEQUENCE: 17

Arg Leu Gly Pro Glu Trp Ser Gln Pro Met Lys Arg
1               5                   10

<210> SEQ ID NO 18
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylated at this location

<400> SEQUENCE: 18

Leu Gly Pro Glu Trp Ser Gln Pro Met Lys Arg
1               5                   10

<210> SEQ ID NO 19
<211> LENGTH: 9
<212> TYPE: PRT
<213> ORGANISM: Homo sapiens

<400> SEQUENCE: 19

Ala Arg Leu Gly Pro Glu Trp Ser Gln
1               5

<210> SEQ ID NO 20
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylated at this location

<400> SEQUENCE: 20

Ala Arg Leu Gly Pro Glu Trp Ser Gln
1               5

<210> SEQ ID NO 21
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylated at this location

<400> SEQUENCE: 21

Ala Arg Leu Gly Pro Glu Trp Ser
1               5
```

```
<210> SEQ ID NO 22
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylated at this location

<400> SEQUENCE: 22

Ala Arg Leu Gly Pro Glu Trp
1               5

<210> SEQ ID NO 23
<211> LENGTH: 17
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: Biotinylated at this location

<400> SEQUENCE: 23

Lys His Pro Phe His Leu Val Ile His Ala Arg Leu Gly Pro Glu Trp
1               5                   10                  15

Ser
```

METHODS FOR SCREENING CANDIDATE AGENTS FOR MODULATING PRORENIN AND RENIN, ASSAYS FOR DETECTING PRORENIN AND ANTIBODIES

CROSS-REFERENCE TO RELATED APPLICATIONS

This application claims the benefit of priority from U.S. Provisional Patent Application Nos. 61/149,834, filed Feb. 4, 2009; 61/150,462, filed Feb. 6, 2009; 61/152,285, filed Feb. 13, 2009; 61/159,233, filed Mar. 11, 2009; 61/160,011, filed Mar. 13, 2009; and 61/234,424, filed Aug. 17, 2009, the contents of all of which are hereby incorporated by reference herein in their entirety.

FIELD OF THE INVENTION

The present invention relates to antibodies that bind to prorenin. In particular, the invention relates to monoclonal antibodies that bind to prorenin and inhibit the activation of prorenin. The antibodies of the invention are useful for screening for candidate agents that inhibit the activation of prorenin and for screening candidate agents that modulate renin activity. The antibodies are also useful as diagnostics and for treating disease states.

BACKGROUND OF THE INVENTION

The aspartyl protease renin is an important modulator of blood pressure. Renin is produced by cleavage of the 395 amino acid zymogen prorenin which circulates in blood at between five and ten times the level of active renin. The putative cleavage site is at the $R^{43}L^{44}$ sequence of prorenin (Mercure et al., *Journal of Biological Chemistry* 270(27): 16355-16359 (1995)).

Human prorenin is easily activated to renin in vitro with catalytic trypsin. A number of enzymes have been suggested as natural activators of prorenin including the cathepsins, plasmin, and various activated coagulation factors (Mercure et al.).

Once activated, renin hydrolyzes angiotensinogen into angiotensin I. Angiotensin I is further processed into angiotensin II by angiotensin converting enzyme (ACE). Angiotensin II is a potent constrictor of blood vessels which then leads to an elevation of blood pressure. Drugs interfering with the renin-angiotensin system (RAS) are currently being widely developed for the treatment of cardiovascular diseases. They not only lower blood pressure, but also prevent end-organ damage. In an attempt to develop drugs to combat high blood pressure, a number of targets including prorenin, ACE, and renin have been developed.

The only currently prescribed renin therapeutic is the recently introduced direct renin inhibitor aliskiren (Novartis Corporation. Basel, Switzerland). However, due to multiple feedback mechanisms within RAS, RAS blockade, including the inhibition of renin, results in the elevation of both renin and its inactive precursor, prorenin. A rise in renin and prorenin occur particularly following treatment with aliskiren (Novartis). The consequences of such increases in renin and prorenin are currently unknown.

However, it is important to note that prorenin is also elevated in plasma of diabetic subjects before the occurrence of complications with nephropathy and retinopathy. Prorenin, like other components of RAS, can also be detected in urine and may provide several advantages. First, urinary prorenin levels may serve as an early marker for diabetic nephropathy and/or retinopathy and facilitate the selection of patients eligible for treatment with a RAS blocker at a very early stage, Early detection and treatment is pertinent in view of the steep rise in diabetes frequency and the devastating consequences of diabetes in eyes and kidneys. Secondly, changes in plasma and/or urinary prorenin levels might help to monitor the response to RAS blockade.

Nonetheless, there are no commercially available sandwich prorenin ELISA assays. Schalekamp et. al. describe a prorenin ELISA assay using a monoclonal antibody directed against the N-terminal prorenin peptide (Schalekamp et al., *Journal of Hypertension* 26:928-937 (2008)). This antibody, produced by F. Hoffmann-La Roche AG (Basel, Switzerland), requires extensive and time consuming pretreatment of the prorenin with a renin inhibitor to remove the propiece from the active site, which makes it reactive and unsuitable for common use.

Accordingly, there is a need for prorenin assays without pretreatment. Such prorenin assays would help to identify (diabetic) patients requiring RAS blockade treatment at a very early stage, thereby greatly reducing the occurrence of nephro- and retinopathy. Prorenin measurements may also allow monitoring of the response to RAS blockade, which may help to ascertain why some patients respond well to RAS blockade whereas others do not. Moreover, such measurements would also help to determine the consequences of the changes in (pro)renin concentrations (e.g., (pro)renin receptor activation) that occur during treatment.

Recently, the so-called prorenin receptor was discovered. It is believed that the effects of increased renin and/or prorenin may be exerted via this receptor. Studies suggest that prorenin may function in the absence of cleavage through its binding to the prorenin receptor. Prorenin exists in two conformations: 1) the open conformation, where the active site is accessible, and 2) the closed conformation, where the active site is not accessible. Binding of prorenin to its receptor results in conformation conversion to the open conformation, resulting in non-proteolytic activation. Nguyen et al., *J. Clin. Invest.* 109: 1417 (2002).

Therefore, there is also the need for methods of inhibiting the activation of prorenin. Such methods may include preventing the cleavage of prorenin to form the active renin or preventing prorenin from binding its receptor, such as by the use of an antibody and/or keeping prorenin in its closed conformation.

SUMMARY OF THE INVENTION

The present invention relates to a monoclonal antibody which binds to prorenin at or near the reactive $R^{43}L^{44}$ bond. Once bound, the antibody has been shown by SDS PAGE to block trypsin from cleaving the zymogen to produce renin. Furthermore, it is believed that the antibody of the invention is capable of locking prorenin in its closed conformation, as well as blocking binding of prorenin to its receptor.

The present invention further relates to a method of modulating the activation of prorenin by administering the antibody of the invention. Methods of treatment by administering the antibody of the invention are also provided, as are humanized antibodies derived from the antibody of the present invention. The antibodies of the invention, and in particular the humanized antibodies of the invention, are useful in treating disease states, such as high cardiovascular disease, blood pressure, diabetes, and disorders associated therewith, in which it is desirable to inhibit prorenin.

It is believed, that based on the ability of the antibody of the invention to bind to prorenin and (1) block trypsin from cleaving prorenin into renin and (2) essentially lock prorenin in its inactive, closed conformation and/or inhibit the binding of prorenin to its receptor, the antibody of the invention is particularly useful in treating disease states.

The antibody of the invention further serves as the basis for development of a new class of therapeutic directly targeting prorenin, which sits upstream in the RAS enzymatic cascade.

In addition, the antibody of the invention serves as the basis for a sandwich prorenin ELISA assay. The assays of the present invention can be used to detect prorenin in biological samples, such as urine and blood.

The invention further relates to a method of screening for molecules that inhibit prorenin activation. The method allows for ease of screening. The method comprises providing the prorenin antibody of the invention, prorenin and a candidate agent to be screened, and determining whether binding of the antibody to prorenin is modulated by the presence of the candidate agent. Once it is determined whether the candidate agent affects binding of the antibody of the invention to prorenin, the candidate agent may be further screened to determine whether it inhibits prorenin activation.

The invention also provides chimeric prorenin polypeptides and nucleic acids encoding the same. In a preferred embodiment, the chimeric prorenin polypeptide of the invention includes a human "pro" region and a non-human renin region. In a preferred embodiment, the non-human renin region is a vertebrate renin region. In a particularly preferred embodiment, the non-human renin region is a rat renin region. The chimeric proteins of the invention can be expressed in various cells, such as in vitro transformed cell lines and/or in vivo in animals. The cell lines and animals should be the same species from which the renin region of the chimeric prorenin is derived.

In a preferred embodiment, transgenic animals stably expressing the chimeric prorenin of the invention are provided. These transgenic animals may be knock-in animals, in which the native prorenin has been replaced with the chimeric protein of the invention. Alternatively, the transgenic animal may express the chimeric prorenin of the invention as well as the native prorenin.

Using the antibody of the present invention, which binds to the pro region of human prorenin, the chimeric prorenin in the transgenic animal and/or cells from the transgenic animal can be studied. For example, prorenin's fate as it binds to its cognate receptor can be followed, as well as its metabolism and half-life. These model systems are also useful in developing diagnostics assays for various diseases associated with prorenin and renin. These model systems are also useful for testing molecules that modulate prorenin, e.g., the antibodies of the present invention, as potential therapeutics for the treatment of disease states in which it is desirable to inhibit prorenin.

BRIEF DESCRIPTION OF THE DRAWINGS

FIG. 3-5 depicts optical density measurements for the screening of peptides to monoclonal antibody 4B5-E3;

FIG. 8 (A) shows the amino acid (SEQ ID NO:1) and (B) nucleotide sequence (SEQ ID NO:2) of human prorenin.

DETAILED DESCRIPTION OF THE INVENTION

Figure 1:
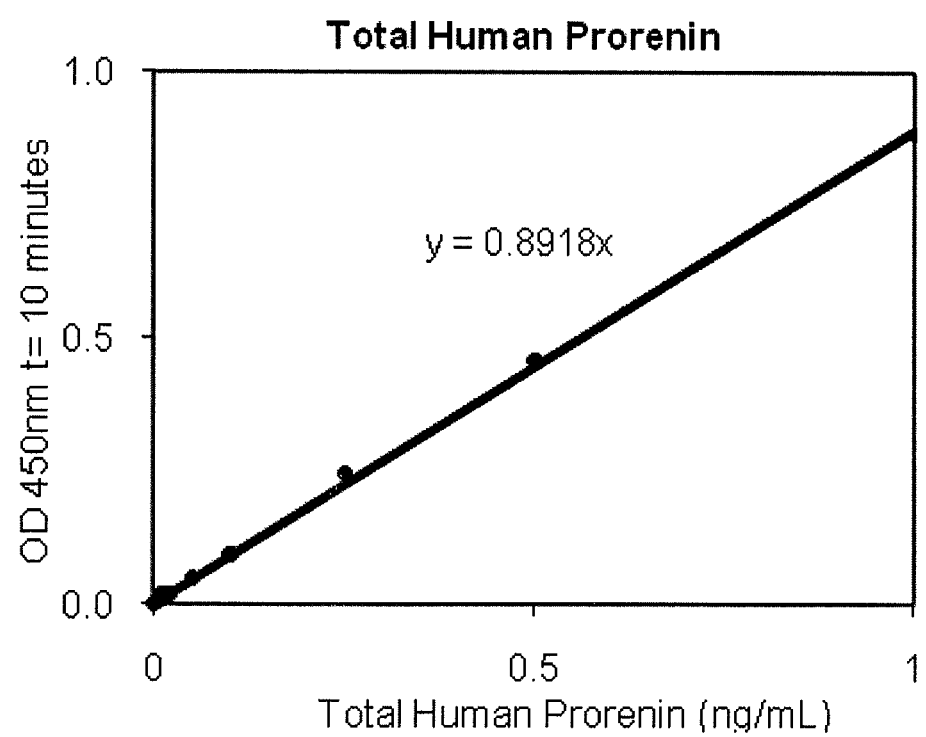
FIG. 1 depicts an exemplary standard calibration curve prepared in the assay of the present invention.

The present invention relates to antibodies that specifically bind to prorenin, thereby inhibiting the activation of prorenin and its binding to the prorenin receptor. The present invention also relates to methods for detecting prorenin using antibodies of the present invention in ELISA assays. The invention disclosed herein further provides for methods of screening candidate agents for modulating the activation of prorenin and candidate agents for modulating the activity of renin. The antibodies disclosed herein are also useful as diagnostics and for treating disease states, such as those associated with high blood pressure, diabetes, and complications of diabetes.

Definitions

In order that the present invention may be more readily understood, certain terms are first defined. Additional definitions are set forth throughout the detailed description and elsewhere in the specification.

The term "antibody" as used herein refers to an immunoglobulin that is reactive to a designated protein or peptide or fragment thereof. Suitable antibodies include, but are not limited to, human antibodies, primatized antibodies, chimeric antibodies, monoclonal antibodies, monospecific antibodies, polyclonal antibodies, polyspecific antibodies, nonspecific antibodies, bispecific antibodies, multispecific antibodies, humanized antibodies, synthetic antibodies, recombinant antibodies, hybrid antibodies, mutated antibodies, grafted conjugated antibodies (i.e., antibodies conjugated or fused to other proteins, radiolabels, cytotoxins), and in vitro-generated antibodies. The antibody can be from any class of antibodies including, but not limited to, IgG, IgA, IgM, IgD, and IgE, and from any subclass (e.g., IgG1, IgG2, IgG3, and IgG4) of antibodies. The antibody can have a heavy chain constant region chosen from, e.g., IgG1, IgG2, IgG3, or IgG4. The antibody can also have a light chain chosen from, e.g., kappa (κ) or lambda (λ). The antibodies of the invention can be derived from any species including, but not limited to mouse, human, camel, llama, fish, shark, goat, rabbit, chicken, and bovine. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function). Typically, the antibody specifically binds to a predetermined antigen, e.g., an antigen associated with a disorder, e.g., disorders related to high blood pressure and diabetes.

The terms "prorenin activity," "activity of prorenin," "prorenin activation," and the like refer to at least one cellular process initiated or interrupted as a result of the cleavage of prorenin to form renin or prorenin binding to the prorenin receptor.

The phrases "inhibit," "antagonize," "block," or "neutralize" prorenin activity or activation and its cognates refer to a reduction, inhibition, or otherwise diminution of at least one activity of prorenin due to binding the prorenin receptor or the cleavage of prorenin to form renin, wherein the reduction, inhibition, or diminution is relative to the activity of prorenin when bound to its receptor or the cleavage of prorenin. Prorenin activity can be measured using any technique known in the art. Inhibition or antagonism does not necessarily indicate a total elimination of the prorenin biological activity. A reduction in activity may be about 10%, 20%, 30%, 40%, 50%, 60%, 70%, 80%, 90%, 95%, or more.

Similarly, the terms "renin activity," "activity of renin," "renin activation," and the like refer to at least one cellular process initiated or interrupted as a result of the hydrolysis of angiotensinogen into angiotensin I.

The phrases "inhibit," "antagonize," "block," or "neutralize" renin activity or activation and its cognates refer to a reduction, inhibition, or otherwise diminution of at least one activity of renin due to binding the hydrolysis of angiotensinogen into angiotensin I. Renin activity can be measured using any technique known in the art. Inhibition or antagonism does not necessarily indicate a total elimination of the renin biological activity. A reduction in activity may be about 10%, 20%, 30%, 40%, 50%, 60%, 70%, 80%, 90%, 95%, or more.

The term "isolated" refers to a molecule that is substantially free of its natural environment. For instance, an isolated protein is substantially free of cellular material or other proteins from the cell or tissue source from which it was derived. The term also refers to preparations where the isolated protein is sufficiently pure for pharmaceutical compositions, or is at least 70-80% (w/w) pure, at least 80-90% (w/w) pure, at least 90-95% (w/w) pure, or at least 95%, 96%, 97%, 98%, 99%, or 100% (w/w) pure.

The phrase "percent identical" or "percent identity" refers to the similarity between at least two different sequences. This percent identity can be determined by standard alignment algorithms, for example, the Basic Local Alignment Search Tool (BLAST) described by Altshul et al., *J. Mol. Biol.* 215:403-10 (1990); the algorithm of Needleman et al., *J. Mol. Biol.* 48:444-53 (1970); or the algorithm of Meyers et al., *Comput. Appl. Biosci.* 4:11-17 (1988). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of Meyers and Miller, *CABIOS* 4:11-17 (1989), which has been incorporated into the ALIGN program (version 2.0), using a PAM120 weight residue table, a gap length penalty of 12, and a gap penalty of 4. The percent identity is usually calculated by comparing sequences of similar length.

The terms "specific binding," "specifically binds," and the like refer to two molecules forming a complex that is relatively stable under physiologic conditions. Specific binding is characterized by a high affinity and a low-to-moderate capacity as distinguished from nonspecific binding, which usually has a low affinity with a moderate-to-high capacity. Typically, binding is considered specific when the association constant Ka is higher than about $10^6 M^{-1} s^{-1}$. If necessary, nonspecific binding can be reduced without substantially affecting specific binding by varying the binding conditions. The appropriate binding conditions, such as concentration of antibody, ionic strength of the solution, temperature, time allowed for binding, concentration of a blocking agent (e.g., serum albumin or milk casein), etc., can be improved by a skilled artisan using routine techniques. Illustrative conditions are set forth herein, but other conditions known to the person of ordinary skill in the art fall within the scope of this invention.

The phrases "substantially as set out," "substantially identical," and "substantially homologous" mean that the relevant amino acid or nucleotide sequence (e.g., CDR(s), $V_H$, or $V_L$ domain(s)) will be identical to or have insubstantial differences (e.g., through conserved amino acid substitutions) in comparison to the sequences which are set out. Insubstantial differences include minor amino acid changes, such as one or two substitutions in a five amino acid sequence of a specified region. In the case of antibodies, the second antibody has the same specificity and has at least about 50% of the affinity of the first antibody.

Sequences substantially identical or homologous to the sequences disclosed herein are also part of this application. In some embodiments, the sequence identity can be about 85%, 90%, 95%, 96%, 97%, 98%, 99%, or higher. Alternatively, substantial identity or homology exists when the nucleic acid segments will hybridize under selective hybridization conditions (e.g., highly stringent hybridization conditions), to the complement of the strand. The nucleic acids may be present in whole cells, in a cell lysate, or in a partially purified or substantially pure form.

As used herein, a "therapeutically effective amount" of an antibody that binds to prorenin refers to an amount of the binding protein that is effective, upon single or multiple dose administration to a subject (such as a human patient) for treating, preventing, curing, delaying, reducing the severity of, and/or ameliorating at least one symptom of a disorder or a recurring disorder, or prolonging the survival of the subject beyond that expected in the absence of such treatment.

Antibodies

The present invention relates to antibodies or fragments thereof that specifically bind to human prorenin, having the amino acid sequence set forth in SEQ ID NO:1 (shown in FIG. 8) and the nucleic acid sequence set for in SEQ ID NO:2 (shown in FIG. 8). In particular, antibodies or fragments thereof of the present invention bind an epitope from the N-terminus of prorenin comprising the 8 amino acids set forth in SEQ ID NO:3. The antibodies of the present invention bind to prorenin at or near the reactive bond $R^{43}L^{44}$, thereby blocking cleavage of the zymogen to renin. In addition, the antibody locks prorenin in its closed conformation, which inhibits the binding of prorenin to the prorenin receptor. In a preferred embodiment, an antibody of the present invention is an anti-human prorenin, such as monoclonal antibody 4B5-E3.

A hybridoma cell line that produces monoclonal antibodies having the properties of monoclonal antibody 4B5-E3 has been deposited at American Tissue Culture Collection (ATCC) on Mar. 26, 2009 in accordance with the Budapest Treaty, and assigned Deposit Designation Number PTA-9894. The address of the depository is 10801 University Blvd, Manassas, Va. 20110, U.S.A. The applicant assures that all restrictions imposed by the depositor on the availability to the public of the deposited material will be irrevocably removed upon the granting of the patent.

Numerous methods known to those skilled in the art are available for obtaining antibodies or fragments thereof. For example, antibodies can be produced using recombinant DNA methods (see, e.g., U.S. Pat. No. 4,816,567). In one embodiment of the invention, the antibodies are monoclonal antibodies. Monoclonal antibodies may also be produced by generation of hybridomas in accordance with known methods (see, e.g., Kohler and Milstein (1975) *Nature* 256:495-99). Hybridomas formed in this manner are then screened using standard methods, such as enzyme-linked immunosorbent assays (ELISA) and surface plasmon resonance (BIA-CORE™) analysis, to identify one or more hybridomas that produce an antibody that specifically binds with a particular antigen. Any form of the specified antigen may be used as the immunogen, e.g., recombinant antigen, naturally occurring forms, any variants or fragments thereof, and antigenic peptides thereof.

In addition, the specified antigen can be used to immunize a nonhuman animal, e.g., a cynomolgus monkey, a chicken, or a rodent (e.g., a mouse, hamster, or rat). In one embodiment, the nonhuman animal includes at least a part of a human immunoglobulin gene. For example, it is possible to engineer mouse strains deficient in mouse antibody production with large fragments of the human Ig loci. Using the hybridoma technology, antigen-specific monoclonal antibodies, derived from the genes with the desired specificity may be produced and selected (see, e.g., XENOMOUSE™ (Amgen Inc., Thousand Oaks, Calif.); Green et al., *Nat. Genet.* 7:13-21 (1994); U.S. Pat. No. 7,064,244; and International Application Publication Nos. WO 96/034096 and WO 96/033735).

In one embodiment of the invention, the antibody is a monoclonal antibody that is obtained from a nonhuman animal, and then modified (e.g., humanized, deimmunized, or chimeric) using recombinant DNA techniques known in the art. A variety of approaches for making chimeric antibodies have been described (see, e.g., Morrison et al., *Proc. Natl. Acad. Sci. USA* 81(21):6851-55 (1985); Takeda et al., *Nature* 314(6010):452-54 (1985); U.S. Pat. Nos. 4,816,567 and 4,816,397; European Application Publication Nos. EP 0 171 496 and EP 0 173 494; and United Kingdom Patent No. GB 2 177 096). Humanized antibodies may also be produced, for example, using transgenic mice that express human heavy and light chain genes, but are incapable of expressing the endogenous mouse immunoglobulin heavy and light chain genes. Winter (U.S. Pat. No. 5,225,539) describes an exemplary CDR-grafting method that may be used to prepare the humanized antibodies described herein. All of the CDRs of a particular human antibody may be replaced with at least a portion of a nonhuman CDR, or only some of the CDRs may be replaced with nonhuman CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or antigen-binding fragments thereof are provided by, e.g., Morrison, *Science* 229:1202-07 (1985); Oi et al., *BioTechniques* 4:214 (1986); and U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antigen is improved by the introduction of conservative substitutions, consensus sequence substitutions, germline substitutions and/or back-mutations. Such altered immunoglobulin molecules can be made by any of several techniques known in the art, (see, e.g., Teng et al., *Proc. Natl. Acad. Sci. USA* 80:7308-73 (1983); Kozbor et al., *Immunol. Today* 4:7279 (1983); Olsson et al., *Meth. Enzymol.* 92:3-16 (1982); International Application Publication No. WO 92/006193; and European Patent No. EP 0 239 400).

In certain embodiments of the invention, the antibody is a single domain antibody. Single domain antibodies include antibodies wherein the CDRs are part of a single domain polypeptide. Examples include, but are not limited to, heavy chain antibodies, antibodies that are naturally devoid of light chains, single domain antibodies derived from conventional four-chain antibodies, engineered antibodies, and single domain protein scaffolds other than those derived from antibodies. Single domain antibodies include any known in the art, as well as any future-determined or -learned single domain antibodies.

Single domain antibodies may be derived from any species including, but not limited to, mouse, human, camel, llama, fish, shark, goat, rabbit, chicken, and bovine. In one aspect of the invention, the single domain antibodies can be derived from a variable region of the immunoglobulin found in fish, such as, for example, that which is derived from the immunoglobulin isotype known as Novel Antigen Receptor (NAR) found in the serum of shark. Methods of producing single domain antibodies derived from a variable region of NAR (IgNARs) are described in, e.g., International Application Publication No. WO 03/014161 and Streltsov, *Protein Sci.* 14:2901-09 (2005). Single domain antibodies also include naturally occurring single domain antibodies known in the art as heavy chain antibodies devoid of light chains. This variable domain derived from a heavy chain antibody naturally devoid of a light chain is known herein as a VHH, or a nanobody, to distinguish it from the conventional $V_H$ of four-chain immunoglobulins. Such a VHH molecule can be derived from antibodies raised in Camelidae species, for example, in camel, llama, dromedary, alpaca, and guanaco, and is sometimes called a camelid or camelized variable domain (see, e.g., Muyldermans (2001) *J. Biotechnol.* 74(4):277-302, incorporated herein by reference). Other species besides those in the family Camelidae may also produce heavy chain antibodies naturally devoid of light chains. VHH molecules are about ten times smaller than IgG molecules. They are single polypeptides and are very stable, resisting extreme pH and temperature conditions. Moreover, they are resistant to the actions of proteases, which is not the case for conventional antibodies. Furthermore, in vitro expression of VHHs can produce high-yield, properly folded functional VHHs. In addition, antibodies generated in camelids will recognize epitopes other than those recognized by antibodies generated in vitro via antibody libraries or via immunization of mammals other than camelids (see, e.g., International Application Publication Nos. WO 97/049805 and WO 94/004678, which are incorporated herein by reference).

The present invention also provides for pharmaceutical compositions comprising antibodies of the present invention and a pharmaceutically acceptable carrier. In addition, therapeutically effective amounts of antibodies of the present invention may be administered to a subject in need thereof for the treatment, prevention, or amelioration of high blood pressure, diabetes, or disorders related to high blood pressure and diabetes.

ELISA Assays

The antibodies of the present invention may be used in ELISA assays for detecting prorenin. In one embodiment, the ELISA assay is a "sandwich" assay. For example, human prorenin and renin (in a biological sample) binds a polyclonal or monoclonal capture antibody, such as sheep anti-human renin antibody (Molecular Innovations Inc., Novi, Mich.) coated on a microtiter plate. After standard washing steps, an antibody of the present invention selectively binds to the captured prorenin. Afterward, the antibody is reacted with the a tagged antibody, such as goat anti-mouse IgG secondary antibody conjugated to horseradish peroxidase, for detection. The "sandwich" formed is the sheep anti-human renin antibody, an antibody of present invention, and the tagged antibody. Alternatively, the antibody of the present invention is the capture antibody that is coated on a microtiter plate. The biological sample comprising prorenin is then contacted with the plate, and the polyclonal or monoclonal anti-human renin antibody is added to bind to the captured prorenin. The tagged antibody for detection is subsequently added to complete the sandwich. Any appropriate substrate for the tagged antibody, such as tetramethylbenzidine (TMB), can be used for color development at the corresponding wavelength, such as 450 nm. A standard calibration curve is prepared along with the samples to be measured using dilutions of prorenin. The amount of color development is directly proportional to the concentration of prorenin in the sample. The assay measures total human prorenin in from about 0.005 ng/ml to about 1.0 ng/ml and has been validated with normal citrated pooled human plasma. A typical standard curve is shown in FIG. 1. The present invention further provides a method for measuring human prorenin in a urine sample, as well as in plasma.

The assay of the present invention is particularly advantageous in that no pretreatment of the sample is necessary. An antibody of the present invention binds to and directly recognizes the previously described prorenin epitope. Only prorenin, and not active renin, will be detected by an antibody of the invention.

Methods of Screening Candidate Agents Capable of Modulating the Activation of Prorenin The present invention provides methods for screening candidate agents capable of modulating the activation of prorenin. For example, an antibody of the present invention can be used in methods for high throughput screening of potential renin inhibitors. In a preferred embodiment, the candidate agent inhibits activation of prorenin. The method includes contacting prorenin with an antibody of the invention separately in the presence and in the absence of the candidate agent under conditions. After the contacting step, the amount of prorenin bound to the antibody is measured. In one embodiment, the prorenin is measured using the ELISA assay of the present invention. The ability of the candidate compound to compete for binding of the antibody to prorenin is determined based on a reduction of binding of the antibody to prorenin. Candidate agents that are capable of inhibiting the binding of the antibody to prorenin are selected to determine whether they are capable of modulating prorenin activation. In a preferred embodiment, the prorenin activation is inhibited. Agents capable of inhibiting prorenin activation may be useful to treat disease states in which it is desirable to inhibit prorenin activation, such as high blood pressure and diabetes.

Methods of Screening Candidate Agents Capable of Modulating the Activity of Renin In a further embodiment of the invention, there is provided a method of screening candidate agents capable of modulating the activity of renin. In a preferred embodiment, the candidate agent inhibits the activity of renin. The method includes contacting a renin substrate with renin separately in the presence and in the absence of candidate agents under conditions wherein renin cleaves the substrate in the absence of the candidate agent. The ability of the candidate compound to modulate renin activity is quantified by measuring the amount of substrate cleaved. This may be accomplished by providing a substrate that is capable of being anchored to an anchoring device. In a preferred embodiment, the anchoring device is a microtiter plate. Alternatively, the anchoring device may be media, such as gel or beads. In one embodiment, the substrate may be anchored to the anchoring device by any means known in the art and once anchored, the substrate may be contacted with renin in the presence and absence of a candidate agent under conditions in which the renin cleaves the substrate. The cleavage of the substrate may be quantified, for example, by linking a measuring epitope to the substrate that provides a detectable signal that is removed when the substrate is cleaved, such as an immunological signal generated from an antibody.

In a preferred embodiment, the substrate includes a peptide which comprises a renin cleavage site derived from angiotensinogen. Such renin-cleavage-site peptides are known in the art, see, e.g., Paschalidou et al., *Biochem J.*, 382:1031-1038 (2004). The substrate may be linked to an anchoring epitope, such as biotin, which can be anchored to an anchoring device. In on embodiment, the substrate peptide has the amino acid sequence of DRVYIHPFHLVIHT (SEQ ID NO:4) and is linked to biotin. In a more preferred embodiment, the substrate peptide has the amino acid sequence of KKHPFHLVIH (SEQ ID NO:5) and is linked to biotin. This substrate peptide is designed to eliminate hydrophobic residues and to include polar residues, which were found to improve solubility and the ability of the peptide to be cleaved.

In a further preferred embodiment, the substrate is linked to a measuring epitope capable of measuring the cleavage of the substrate peptide. The measuring epitope may be any epitope having a signal that is removed when the substrate is cleaved. Thus, measurement of cleavage is achieved by measuring the loss of the signal generated by the measuring epitope. In a preferred embodiment, the measuring epitope is an immunological measuring epitope, such as an epitope that is recognized by an antibody. In a preferred embodiment, the measuring epitope is a peptide of the invention that is recognized by an antibody of the invention. In a particularly preferred embodiment, the measuring epitope has the amino acid sequence selected from the group consisting of ARLGPEWS (SEQ ID NO:6) and ARLGPEW (SEQ ID NO:7).

Thus, in accordance with a particularly preferred embodiment, the present invention provides a method of identifying candidate agents capable of inhibiting renin activity comprising contacting a substrate peptide having the amino acid sequence KHPFHLVIHARLGPEWS (SEQ ID NO:8) or KHPFHLVIHARLGPEW (SEQ ID NO:9) with renin in the presence or absence of a candidate agent, wherein the peptide is preferably linked to biotin, and determining the amount of cleavage of the peptide by renin. The peptide is preferably linked to an anchoring device, such as a microtiter plate coated with avidin, via the biotin. In addition, the peptide is preferably linked to a measuring epitope. The cleavage of the peptide is preferably measured by contacting the peptide with the antibody of the invention that is capable of recognizing the measuring epitope. In a preferred embodiment, the measuring epitope comprises an amino acid sequence ARLGPEWS (SEQ ID NO:6) and ARLGPEW (SEQ ID NO:7). The presence of bound antibody is measured by any means known in the art and preferably provides a color indicator. If the substrate peptide of the invention is cleaved, the measuring epitope is removed and the antibody will not bind to it, thus, no color will be detected.

EXAMPLES

The invention will be further illustrated in the following nonlimiting examples. These Examples are set forth to aid in the understanding of the invention but are not intended to, and should not be construed to, limit its scope in any way. The Examples do not include detailed descriptions of conventional methods that would be well known to those of ordinary skill in the art.

Example 1

Monoclonal Antibody Production

Several BALB/c female mice were used for this project. For primary immunization, Mice were 6 weeks old. Physiological soluble human prorenin was purchased from Proteos, Inc. (Kalamazoo, Mich.).

Prorenin was emulsified in the complete Freund's adjuvant (CFA) for initial immunization. There were three additional boosts at 2-3 weeks intervals with incomplete Freund's adjuvant (IFA). Blood was collected for sera ELISA testing 5-7 days after injection to determine the titer. The final boost was done 3 days before the cell fusion. The mouse with the highest titer was chosen for the spleen cell harvest.

Mouse myeloma cells were purchased from ATCC. Spleen cells were added to the myeloma cells at a ratio of 5 spleen cells per myeloma cell with PEG solution to assist in the fusion. The cells were cultured in 96 wells plates in Iscove's Modified Dulbecco's Media (IMDM) (Fisher Scientific, Pittsburgh, Pa.) with 20% fetal bovine serum (FBS), L-Glutamine, Pen/Strep, Hybridoma Cloning Supplement (HCS) and hypoxanthine and thymidine (HT). Aminoptrin was added at day 2 and one week after the fusion to remove unfused myeloma cells.

Cell clones appeared at about 2 weeks. Supernatant was tested based on the clone growth and the media pH change. Positive clones were expanded to 24 wells cell culture plates.

Limiting dilution was used for the subcloning. After 10 days of subcloning, the wells were marked with only a single growing colony of cells, the supernatant was screened with ELISA and Western blot, and the antibodies were isotyped.

Immobilized Protein-A was used for the monoclonal antibody purification.

Example 2

Characterization of Prorenin Mouse Monoclonal Antibody 4B5-E3

Example 2.1

ISOSTRIP™ Mouse Monoclonal Antibody Isotyping Kit

The monoclonal antibody 4B5-E3 was characterized using the ISOSTRIP™ Mouse Monoclonal Antibody Isotyping Kit (Roche Applied Science, Indianapolis, Ind.). ISOSTRIP™ includes two components: 1) colored latex beads that bear anti-mouse kappa and anti-mouse lambda antibodies, which will react with any mouse antibody, and 2) isotyping strip bearing immobilized bands of goat anti-mouse antibodies' corresponding to each of the common mouse antibody isotypes. The strip also includes control bands. Diluted sample mouse monoclonal antibody is added to a development tube that contains the colored latex beads in which the sample mouse monoclonal antibody forms a complex with the antibody-coated beads. When the isotyping strip is placed in the development tube, the complex flows up the strip by capillary action until it is bound by the immobilized goat anti-mouse antibody specific for the sample monoclonal's isotype. Using ISOSTRIP™, the monoclonal antibody 4B5-E3 of the invention was determined to be IgG immunoglobulin, subclass 2b with kappa-light chain.

Example 2.2

Western Blotting

Figure 2:
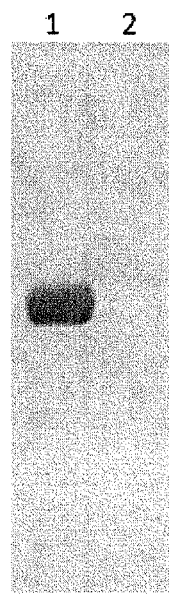
FIGS. 2-4 shows a Western blot of human prorenin in lane 1 and human prorenin incubated with catalytic trypsin in lane 2.

It was determined from the western blotting of human prorenin (FIG. 2) that the antibody 4B5-E3 blotted only the proform of the enzyme. Therefore, it was determined that the epitope of monoclonal must be within the first 43 amino acids which occur N-terminal to the putative cleavage site. The prorenin sample (1 ml at 1 mg/ml) in lane 1 was incubated in 0.1M Tris-0.15M NaCl—pH 8.0 (TBS) with catalytic trypsin (0.5 ml of 1:1 slurry) for 10 minutes and run in lane 2 (0.5 µg was loaded in each lane of each sample respectively). The Western Blot was blotted with the primary antibody at 1 µg/ml and the secondary antibody at 1:3000. There is no evidence of any binding to active renin.

Example 3

Monoclonal Antibody Screening

Cell supernatants were loaded on an IMMULON™ (Thermo Fisher Scientific Inc., Waltham, Mass.) strip plate coated with prorenin and blocked. After 30 minutes of shaking the plate at room temperature, the supernatants were aspirated off the plate, strips were washed in 1× wash buffer three times, and the strips were incubated with a peroxidase-conjugated affinity purified goat anti-mouse IgG to subclasses 1+2a+2b+3, Fc fragment-specific antibody for 30 minutes. Strips were then washed three times, and developed with TMB 1 (Kirkegaard & Perry Laboratories, Inc., Gaithersburg, Md.) substrate for 5 minutes; solution was quenched with 1N $H_2SO_4$. The IMMULON™ plate was read on a microtiter plate spectrophotometer with a set absorbance at 450 nm. Optical density (OD) measurements higher than 3.0 were considered positive clones.

Four biotinylated synthetic peptides (Biosynthesis Inc., Lewisville, Tex.) were made corresponding to the N-terminal 43 amino acid sequence of prorenin shown below: (43 aa sequence) LPTDTTTFKRIFLKRMPSIRESLKERGVDMARLGPEWSQPMKR (SEQ ID NO:10)

```
Peptide 1)
                                             (SEQ ID NO: 11)
    Biotin-LPTDTTTFKRIFLKR Peptide 2)
                                             (SEQ ID NO: 12)
    Biotin-TDTTTFKRIFLKRMP Peptide 3)
                                             (SEQ ID NO: 13)
    Biotin-KRMPSIRESLKERGVDM Peptide 4)
                                             (SEQ ID NO: 14)
    Biotin-GVDMARLGPEWSQPMKR (binds monoclonal)
```

These four peptides were bound to avidin coated plates at a concentration of 1 µg/ml and purified monoclonal 4B5-E3 binding was determined per the screening procedure described earlier.

Figure 3:
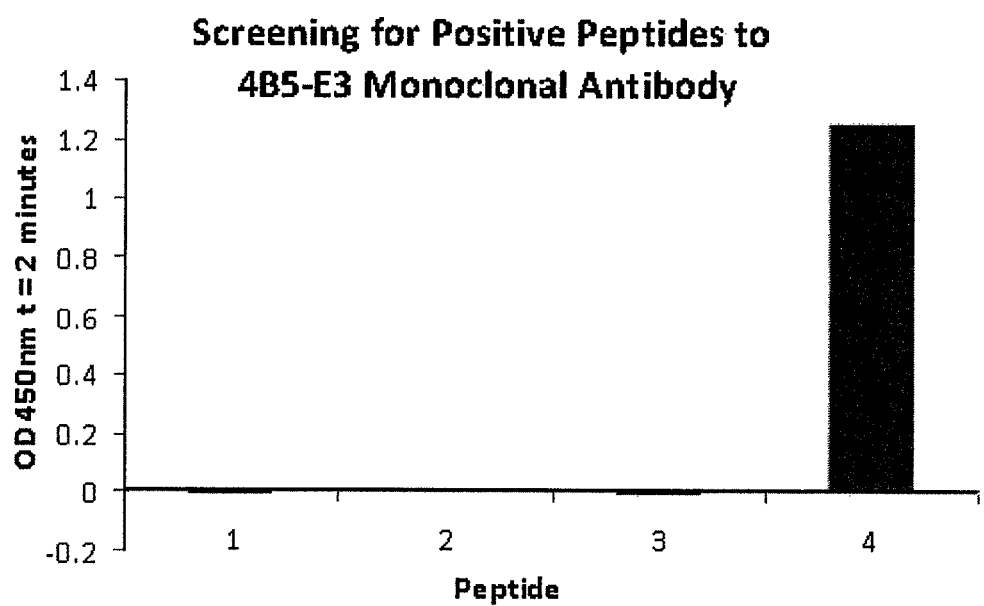

As shown in FIG. 3 below, only peptide 4 gave a positive result with the monoclonal antibody. Based on this result it was possible to further narrow the epitope for the 4B5-E3 monoclonal antibody to residues 30-43 (MARLGPEWSQPMKR; SEQ ID NO:15). Since the monoclonal antibody was made to intact human prorenin, it is possible that the epitope spans the cleavage site.

This peptide was further narrowed by testing the following 3 peptides derived from peptide 4:

```
Peptide 4.1)
                                             (SEQ ID NO: 16)
    Biotin-ARLGPEWSQPMKR (binds monoclonal)
```

-continued

```
Peptide 4.2)
                                        (SEQ ID NO: 17)
Biotin-RLGPEWSQPMKR (binds monoclonal)

Peptide 4.3:
                                        (SEQ ID NO: 18)
Biotin-LGPEWSQPMKR (does not bind monoclonal)
```

Figure 4:
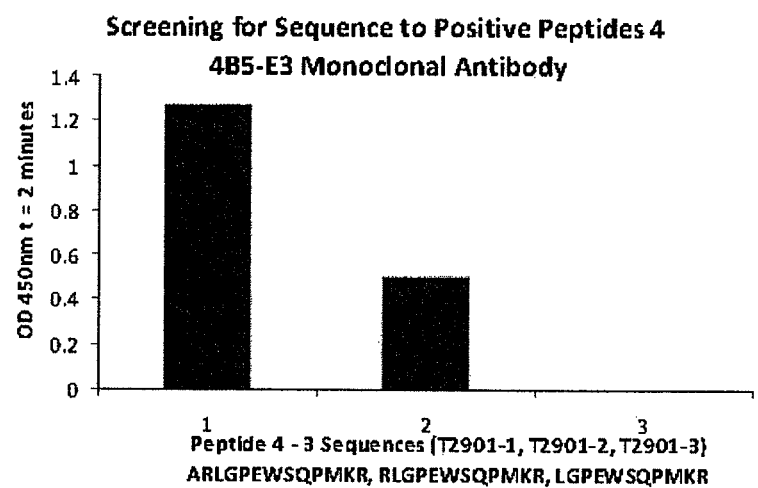

The results for these peptides is shown in FIG. 4 below.

Further narrowing of this peptide led to the discovery that residues 31-38 and 31-39 (ARLGPEWS (SEQ ID NO: 6) and ARLGPEWSQ, (SEQ ID NO:19 respectively), bound to the monoclonal antibody. As shown in FIG. 5 below, this was determined by testing the following 3 peptides:

Peptide 4.4) Biotin-ARLGPEWSQ (binds monoclonal) (SEQ ID NO:20)

Peptide 4.5) Biotin-ARLGPEWS (binds monoclonal) (SEQ ID NO:21)

Peptide 4.6) Biotin-ARLGPEW (does not bind monoclonal) (SEQ ID NO:22).

Example 4

Detection of Human Prorenin in a Human Urine Sample

Figure 6A:
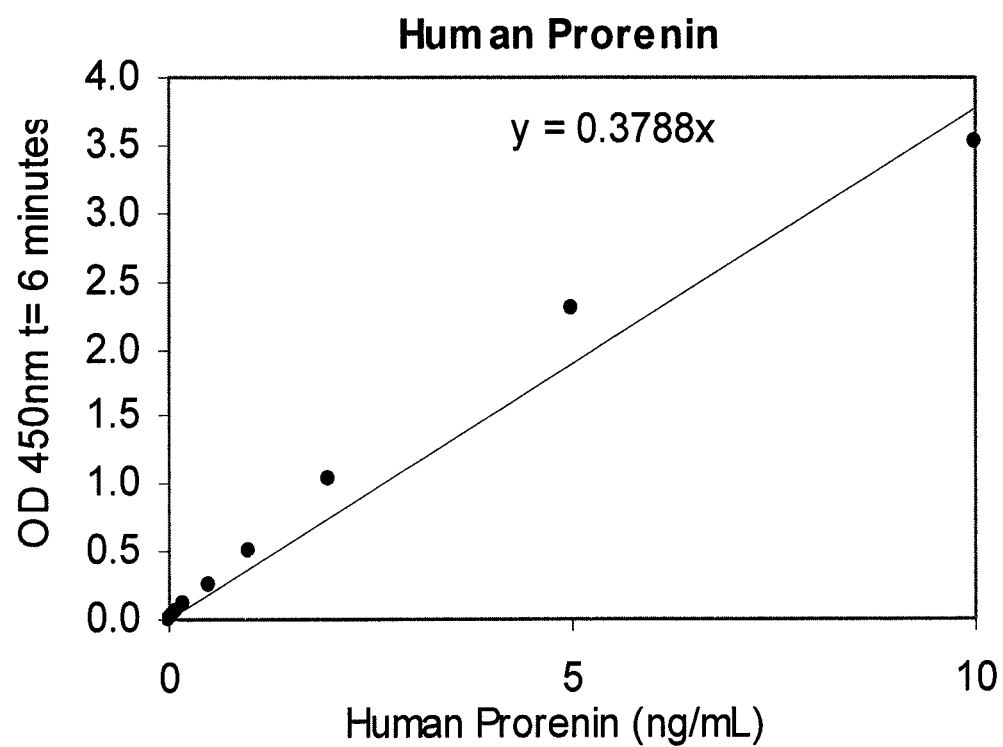
FIG. 6A-C show results from the detection of prorenin in urine samples.
Figure 6B:
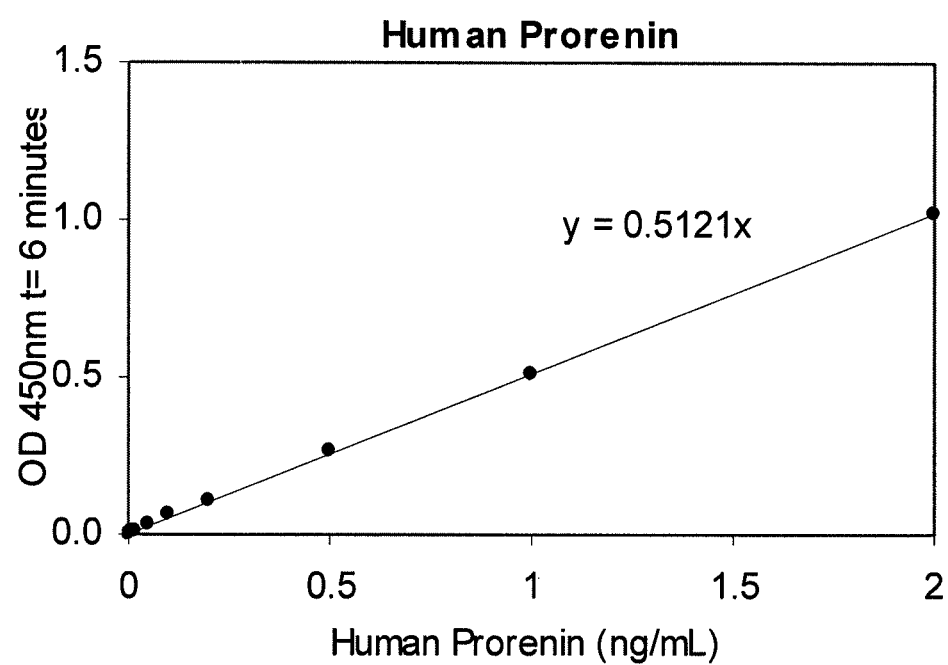
Figure 6C:
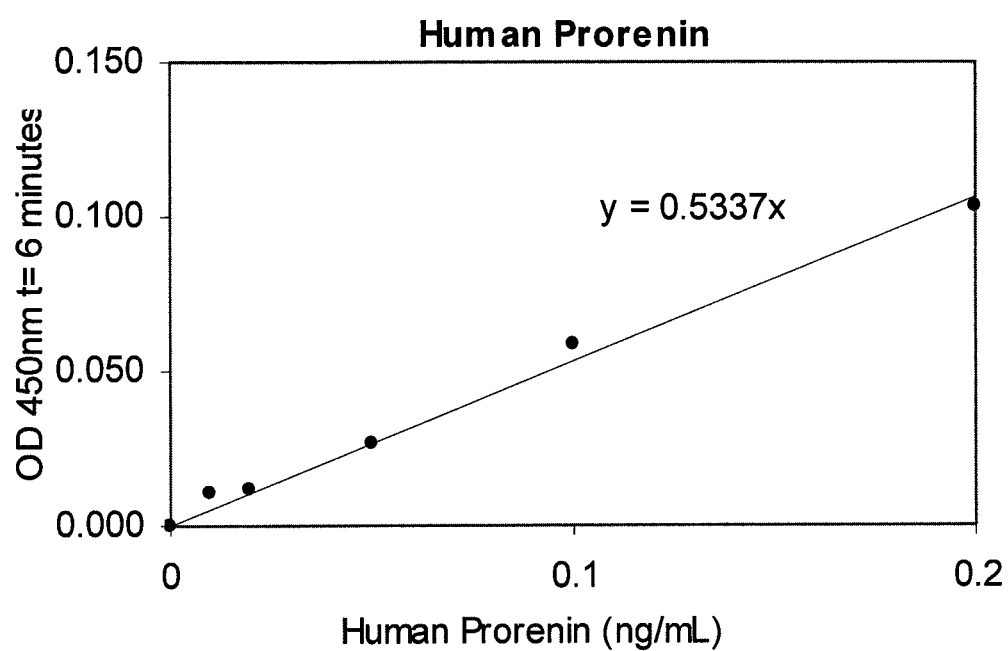

The data provided below show that prorenin was detected in two human urine samples, labeled BL and NSB. The assay was conducted by binding a polyclonal sheep anti-human renin to a microtiter plate, incubating a urine sample in the microtiter plate coated with the antibody to capture any pro-renin/renin in the urine sample, washing the plate to remove residual urine sample, incubating any captured prorenin/renin with the anti-human prorenin antibody of the invention and detecting the binding of the antibody of the invention to the captured sample. Any signal detected relates to the presence of prorenin in the sample. Concentration of the urine sample, resulted in a correlative increase in the signal obtained. The data obtained from the urine samples is provided below in FIGS. 6A-C.

Example 5

Modulating Prorenin Activity

Figure 7:
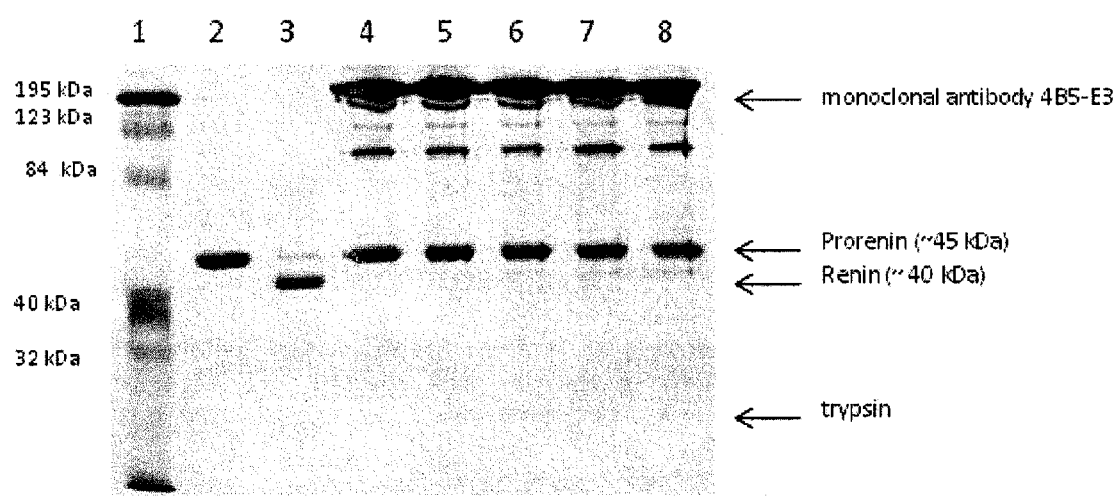
FIG. 7 shows SDS PAGE results of prorenin incubated without or with catalytic trypsin (lanes 2 and 3, respectively) and prorenin pre-incubated with monoclonal antibody 4B5-E3, followed by the addition of catalytic trypsin at 1, 3, 5, 10, and 30 minute intervals (lanes 4-8, respectively)

Because the epitope was shown to be linear and not conformational and that binding is at or very near the scissile bond $R^{43}L^{44}$, an experiment was set up to determine if the monoclonal antibody 4B5-E3 was capable of sterically blocking enzymatic activation of prorenin. Prorenin at a concentration of 0.5 mg/ml was incubated without or with catalytic trypsin in TBS buffer (Lanes 2 and 3 respectively) for 1 minute (see FIG. 7). Prorenin at a concentration of 0.5 mg/ml was then pre-incubated with the monoclonal antibody 4B5-E3 at a concentration of 1 mg/ml followed by addition of catalytic trypsin. Samples were taken at 1, 3, 5, 10 and 30 minute intervals (Lanes 4-8) and run on non reducing SDS PAGE. Molecular weight standards were run in lane 1.

This experiment demonstrates that the monoclonal antibody 4B5-E3 protects prorenin from enzymatic cleavage by trypsin over the time course of the experiment and may serve as the basis of a therapeutic agent in the blockage of renin generation.

Example 6

Modulation of Renin Activity

In accordance with the invention, renin was preincubated in the presence and absence of aliskiren, a known renin inhibitor for approximately 2 hours at 37° C. in 50 mM HEPES, 2 mM EDTA, 1% DMA, 0.5% BSA, pH 7.0. This mixture of renin +/−aliskiren was then contacted with biotin-KHPF-HLVIHARLGPEWS and incubated at 37° C. for approximately eighteen hours. The reaction mixture was then added to an avidin-coated microtiter plate and allowed to adhere thereto for 30 minutes at room temperature and then washed three times with wash buffer, containing 10 mM Tris, 150 mM NaCl, 0.1% BSA and 0.05% Tween. Then 100 µl of the antibody of the invention was added to each well of the microtiter plate and incubated for 30 minutes at room temperature and again washed with wash buffer. Then 100 µl of horse radish peroxidase conjugated goat anti-mouse subclass Fc was added to each well, incubated for 30 minutes at room temperature and washed with wash buffer. Then 100 µl of TMB ONE Solution™, available from Promega Corporation of Madison, Wis., was added to all wells, incubated for five minutes at room temperature. The reaction was stopped with 50 µl 1N H2SO4 and read at 450 nM.

Table I shows the results from the assay, showing that the presence of aliskiren resulted in the inhibition of cleavage of the substrate peptide by renin.

TABLE I

| B | R + I | R + I | R + I | R | R | R | P | P | P |
|---|-------|-------|-------|---|---|---|---|---|---|
| 0.043 | 3.363 | 3.481 | 3.596 | 0.098 | 0.107 | 0.091 | 3.429 | 3.436 | 3.398 |
| 0.043 | 3.824 | 3.754 | 3.497 | 0.149 | 0.161 | 0.145 | 3.898 | 4 | 3.808 |

B = Blank
R = Renin at 10 ug/ml
I = Inhibitor aliskiren at 10X excess molar conc.
P = peptide only

I claim:

1. A method for detecting human prorenin comprising:
   a. first contacting an untreated sample with a capture antibody coated on an anchoring device;
   b. adding an antibody that is capable of binding to an amino acid sequence selected from the group consisting of SEQ ID NO:3, SEQ ID NO:6 and SEQ ID NO:7, wherein the antibody is capable of sterically blocking enzymatic activation of prorenin;
   c. reacting the anti body with a tagged antibody; and
   d. detecting the level of human prorenin in the sample;
   wherein the antibody is 4B5-E3, having ATCC Deposit Designation Number PTA-9894.

2. A method for determining the ability of a candidate agent to inhibit renin activity comprising:
   a. providing a substrate having a renin cleavage site and a measuring epitope;
   b. contacting a substrate with a sample comprising renin in the presence of the candidate agent;
   c. contacting a substrate with a sample comprising renin in the absence of the candidate agent;
   d. contacting the substrate in step (b) and in step (c) with an antibody that binds to the measuring epitope; and
   e. measuring an amount of substrate cleaved in steps (b) and (c);
   wherein the amount of the substrate cleaved in step (b) being significantly less than the amount of the substrate cleaved in step (c) indicates that the candidate agent is able to inhibit renin activity, wherein the measuring epitope comprises an amino acid sequence derived from human prorenin, wherein the measuring epitope comprises an amino acid sequence selected from the group consisting of SEQ ID NO:3, SEQ ID NO:6 and SEQ ID NO:7, wherein the antibody is capable of binding to at least one of said amino acid sequences and capable of sterically blocking enzymatic activation of prorenin, and wherein the antibody is 4B5-E3, having ATCC Deposit Designation Number PTA-9894.

3. The method of claim 2, wherein the substrate is anchored to an anchoring device by biotin.

4. The method of claim 2, wherein the substrate comprises an amino acid sequence selected from the group consisting of SEQ ID NOs:4 and 5.

5. The method of claim 2, wherein the measuring epitope comprises an amino acid sequence selected from the group consisting of SEQ ID NOs: 6 and 7.

6. A method for determining the ability of a candidate agent to inhibit prorenin activation comprising:
   a. contacting an antibody capable of binding to an amino acid sequence selected from the group consisting of SEQ ID NO: 3, SEQ ID NO:6 and SEQ ID NO:7 with a sample comprising prorenin in the presence of the candidate agent;
   b. contacting the antibody with a sample comprising prorenin in the absence of the candidate agent; and
   c. measuring an amount of bound antibody in steps (a) and (b);
   wherein the antibody binds to human prorenin, wherein the antibody is capable of sterically blocking enzymatic activation of prorenin, and wherein the amount of bound antibody in step (a) being significantly less than the amount of the antibody bound in step (b) indicates that the candidate agent is able to inhibit prorenin activation, and wherein the antibody is 4B5-E3, having ATCC Deposit Designation Number PTA-9894.

7. The method of claim 6, wherein a capture antibody is coated on an anchoring device.

8. The method of claim 7, wherein the capture antibody is a sheep anti-human renin antibody.

9. The method of claim 4 or 7, wherein the anchoring device is selected from the group consisting of a microtiter plate, a gel, and beads.

10. The method of claim 7, wherein the antibody is reacted with a tagged antibody.

11. The method of claim 10, wherein the tagged antibody is goat anti-mouse IgG secondary antibody conjugated to horseradish peroxidase.

12. The method of claim 6, wherein the antibody is coated on an anchoring device.

13. The method of claim 6, wherein the method further comprises contacting the sample with a capture antibody.

14. The method of claim 13, wherein the capture antibody is reacted with a tagged antibody.

15. The method of claim 14, wherein the tagged antibody is goat anti-mouse IgG secondary antibody conjugated to horseradish peroxidase.

16. An antibody that binds to an amino acid sequence selected from the group consisting of SEQ ID NO:3, SEQ ID NO:6 and SEQ ID NO:7, wherein the antibody is capable of sterically blocking enzymatic activation of prorenin, and wherein the antibody is 4B5-E3, having ATCC Deposit Designation Number PTA-9894.

17. A method of treating or ameliorating cardiovascular disease, high blood pressure, or diabetes comprising administering the antibody of claim 16.

18. A pharmaceutical composition comprising the antibody of claim 16.

* * * * *